(12) United States Patent
Ootsuki et al.

(10) Patent No.: US 9,558,552 B2
(45) Date of Patent: Jan. 31, 2017

(54) EYE-FUNDUS IMAGE OPTIMIZATION OUTPUT DEVICE AND METHOD, AND COMPUTER READABLE MEDIUM

(71) Applicant: Sony Corporation, Tokyo (JP)

(72) Inventors: Tomoyuki Ootsuki, Kanagawa (JP); Seiji Kobayashi, Tokyo (JP); Kazuki Aisaka, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/646,545

(22) PCT Filed: Feb. 10, 2014

(86) PCT No.: PCT/JP2014/053002
§ 371 (c)(1),
(2) Date: May 21, 2015

(87) PCT Pub. No.: WO2014/129339
PCT Pub. Date: Aug. 28, 2014

(65) Prior Publication Data
US 2015/0302582 A1    Oct. 22, 2015

(30) Foreign Application Priority Data

Feb. 22, 2013  (JP) ................. 2013-033494

(51) Int. Cl.
*G06K 9/00* (2006.01)
*G06T 7/00* (2006.01)
(Continued)

(52) U.S. Cl.
CPC ............. *G06T 7/0012* (2013.01); *A61B 3/12* (2013.01); *A61B 3/14* (2013.01); *G06K 9/0061* (2013.01);
(Continued)

(58) Field of Classification Search
None
See application file for complete search history.

(56) References Cited

U.S. PATENT DOCUMENTS 5,270,924 A * 12/1993 Hideshima ............... A61B 3/12
382/117
7,583,827 B2 * 9/2009 Hansen ................. G06T 7/0012
382/128
(Continued)

FOREIGN PATENT DOCUMENTS

JP    8-66365 A    3/1996
JP    11-238129 A    8/1999
(Continued)

OTHER PUBLICATIONS

'Adjusting a Selected Area,' from Adobe Photoshop CS5 Techniques for Photographers: Learn by Video [online]. [retrieved on Apr. 1, 2016]. Retrieved from the Internet: https://www.video2brain.com/en/lessons/adjustingaselectedarea].*
(Continued)

*Primary Examiner* — Jason Heidemann
(74) *Attorney, Agent, or Firm* — Oblon, McClelland, Maier & Neustadt, L.L.P.

(57) ABSTRACT

An eye-fundus image output device, including circuitry to: select a site of a presented eye-fundus image, optimize an image of the selected site, output an image in which the selected site has been optimized, and generate a graphical user interface (GUI) corresponding to a received instruction, the GUI selects, as a grayscale adjustment mode, a mode in which a selected portion of an image of a predetermined range in the periphery of a designated position is optimized according to the grayscale adjustment mode.

12 Claims, 18 Drawing Sheets

(51) Int. Cl.
*A61B 3/14* (2006.01)
*A61B 3/12* (2006.01)
*G06T 5/00* (2006.01)
*G09G 5/10* (2006.01)

(52) U.S. Cl.
CPC .............. *G06T 5/00* (2013.01); *G06T 7/004* (2013.01); *G09G 5/10* (2013.01); *G06T 2207/30041* (2013.01)

(56) References Cited

U.S. PATENT DOCUMENTS

| | | | |
|---|---|---|---|
| 8,355,544 B2* | 1/2013 | Gomez-Ulla de Irazazabal | G06K 9/0061 351/209 |
| 2010/0238403 A1* | 9/2010 | Kobayashi | A61B 3/0058 351/206 |
| 2012/0189184 A1* | 7/2012 | Matsumoto | A61B 3/102 382/131 |
| 2013/0063698 A1* | 3/2013 | Akiba | A61B 3/12 351/206 |
| 2013/0321765 A1* | 12/2013 | Yuasa | A61B 3/1025 351/206 |
| 2013/0321766 A1* | 12/2013 | Morohashi | A61B 3/1025 351/206 |
| 2013/0321768 A1* | 12/2013 | Utagawa | A61B 3/1025 351/206 |
| 2013/0321771 A1* | 12/2013 | Yuasa | A61B 3/1025 351/208 |
| 2014/0240673 A1* | 8/2014 | Iwanaga | A61B 3/12 351/207 |

FOREIGN PATENT DOCUMENTS

| | | |
|---|---|---|
| JP | 2000-197608 A | 7/2000 |
| JP | 2001-137191 A | 5/2001 |
| JP | 2003-52639 A | 2/2003 |
| JP | 2003-299620 A | 10/2003 |
| JP | 2004-298488 A | 10/2004 |
| JP | 2005-6890 A | 1/2005 |
| JP | 2008-295804 A | 12/2008 |
| JP | 2010-158279 A | 7/2010 |
| JP | 2010-246904 A | 11/2010 |
| JP | 2011-31027 A | 2/2011 |

OTHER PUBLICATIONS

'ImageJ Brightness/contrast selection in grayscale images' [online]. [retrieved on Apr. 1, 2016]. Retrieved from the Internet: http://imagej.1557.x6.nabble.com/Brightnesscontrastselectioningrayscaleimagestd3689259.html].*

Ferreira et al., "Chapter 29—Process" from "ImageJ User Guide IJ 1.46r", Published: Tuesday Oct. 2, 2012, pp. 107-110.*

International Search Report issued May 13, 2014 in PCT/JP2014/053002 (with English language translation).

* cited by examiner

EYE-FUNDUS IMAGE OPTIMIZATION OUTPUT DEVICE AND METHOD, AND COMPUTER READABLE MEDIUM

TECHNICAL FIELD

The present technology relates to an eye-fundus image output device and method, and a program, and particularly to an eye-fundus image output device and method, and a program which enable an image in which a desired site of an eye fundus is easy to view to be output quickly.

BACKGROUND ART

Different sites of an eye fundus of a human being significantly vary in brightness, and for example, a macular area is dark and an optic disc portion is quite bright in comparison to other portions. For this reason, when the eye fundus is presented on a display with brightness at which the macular area is easily observed, an image of the optic disc portion becomes completely white. Conversely, when the eye fundus is presented with brightness at which the optic disc portion is easily observed, an image of the macular area and the like becomes completely black in most cases. This phenomenon has been an obstacle in diagnosis using eye-fundus images for a long period of time. The complete whiteness and blackness described above are attributable to an insufficient dynamic range of an image sensor when an image is photographed and an insufficient dynamic range of a display that presents an eye-fundus image.

As a method for overcoming the insufficient dynamic range of an image sensor, for example, combining images photographed a plurality of times under different exposure conditions has been proposed (Patent Literature 1). However, even though an image with a sufficient dynamic range for expressing an eye fundus is obtained using the method, if the dynamic range of a display which expresses the image is insufficient, the image to be expressed becomes completely white or completely black after all.

As a method for overcoming an insufficient dynamic range of a display, for example, allocating more levels of a grayscale to a target site to be noted than to other portions when the grayscale of an input image is corrected has been proposed (Patent Literature 2). In addition, when there are a plurality of sites to be noted, for example, generating and storing a plurality of images in which the respective sites are easily viewed in a stage in which the images are to be stored has been proposed (Patent Literature 3).

CITATION LIST

Patent Literature

Patent Literature 1: JP 2011-31027A
Patent Literature 2: JP 2000-197608A
Patent Literature 3: JP 2003-52639A

SUMMARY OF INVENTION

Technical Problem

In the proposals, however, prior to interpretation of radiography of the image by a doctor, a photographer should decide a site to be noted and an adjustment method of the image based on the site in advance. As a result, at the time not of photographing but of interpretation, it is not possible for the doctor or the like to adjust the image so that he or she can easily observe it according to the site to be noted. More specifically, it is difficult to adjust the image while sequentially changing the site to be noted in real time.

The present technology takes the above circumstances into consideration, and aims to enable an image in which a desired site of an eye fundus is easily viewed to be output quickly.

Solution to Problem

According to an aspect of the present disclosure, there is provided an eye-fundus image output device including: a selection unit configured to select a site of a presented eye-fundus image; an optimization unit configured to optimize an image of the selected site; and an output unit configured to output an image in which the selected site has been optimized.

A generation unit can be further included, the generation unit being configured to generate a presentation image that is obtained by combining a GUI that includes a manipulation unit that is manipulated by a user when a plurality of grayscale adjustment modes are to be set with the eye-fundus image.

The GUI can select, as the grayscale adjustment modes, at least two of a mode in which the site is selected, a mode in which an image of a predetermined range in the periphery of the designated position is optimized, or a mode in which an optimization value of the image is designated.

The GUI can include a manipulation unit that is manipulated when at least a macular area or an optic disc portion is selected as the site in the mode in which the site is selected.

When the mode in which an image in the periphery of the designated position is optimized is selected as the grayscale adjustment mode, the optimization unit can optimize the image of the predetermined range in the periphery of the designated position.

When the mode in which an optimization value of the image is designated is selected as the grayscale adjustment mode, the optimization unit can optimize the image to have the designated optimization value.

In the mode in which an optimization value of the image is designated, the GUI can include a manipulation unit that is manipulated when the optimization value is to be designated.

In the mode in which an optimization value of the image is designated, the manipulation unit that is manipulated when the optimization value of the image is designated can be disposed at a position corresponding to a value disposed in the immediately previous grayscale adjustment mode.

The position corresponding to the value disposed in the immediately previous grayscale adjustment mode of the manipulation unit can be set to a center of a variable range.

The optimization can be performed by adjusting brightness or contrast of the image.

According to an aspect of the present disclosure, a selection unit selects a site of a presented eye-fundus image, an optimization unit optimizes an image of the selected site; and an output unit outputs an image in which the selected site has been optimized.

A method and a program according to an aspect of the present technology are a method and a program that correspond to an eye-fundus image output device of an aspect of the present technology described above.

Advantageous Effects of Invention

As described above, according to an aspect of the present technology, it is possible to quickly output an image in which a desired site of an eye fundus is easily visible.

DESCRIPTION OF EMBODIMENTS

Figure 1:
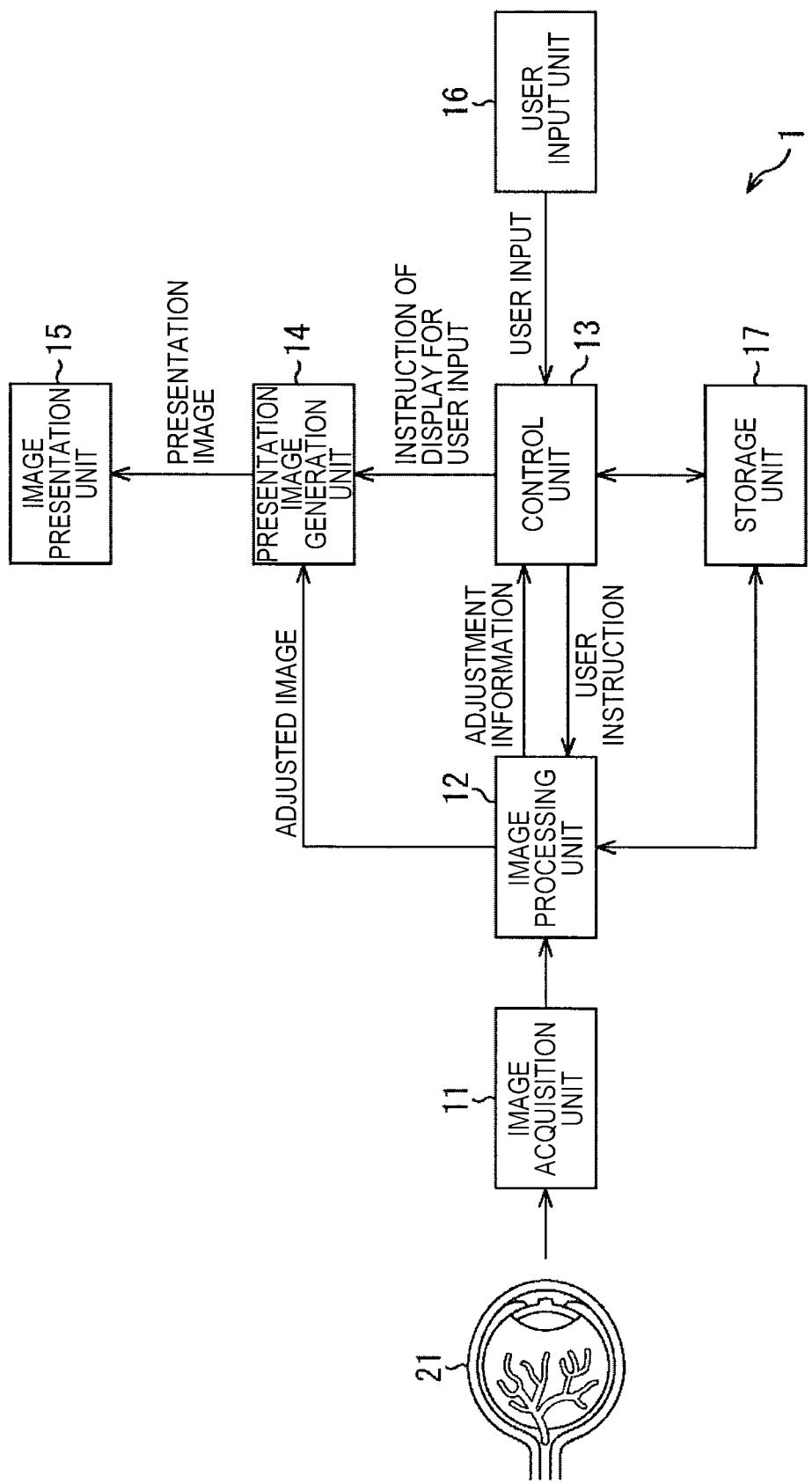
FIG. 1 is a block diagram illustrating a configuration of an embodiment of an eye-fundus image output device of the present technology.

Hereinafter, modes for carrying out the present technology (hereinafter referred to as embodiments) will be described. It should be noted that description will be provided in the following order.

1. Configuration of an eye-fundus image output device
2. Image display process
3. Configuration of an image processing unit
4. Optimization process of a set mode
5. Site selection mode
6. Adjustment of gain and contrast
7. Pointing mode
8. Slider mode
9. Application to a program of the present technology
10. Other configurations

[Configuration of an Eye-Fundus Image Output Device]

FIG. 1 is a block diagram illustrating a configuration of an embodiment of an eye-fundus image output device 1 of the present technology. The eye-fundus image output device 1 is constituted by an image acquisition unit 11, an image processing unit 12, a control unit 13, a presentation image generation unit 14, an image presentation unit 15, a user input unit 16, and a storage unit 17.

The image acquisition unit 11 has, for example, a charge coupled device (CCD) image sensor, a complementary metal oxide semiconductor (CMOS) image sensor, or the like to capture an eye-fundus image of a subject eye 21 of an examinee. The image acquired by the image acquisition unit 11 is supplied to the image processing unit 12 in real time. The image processing unit 12 is configured as, for example, a digital signal processor (DSP), which performs an optimization process on the input image from the image acquisition unit 11 based on a user instruction from the control unit 13 and outputs a result of the process as an adjusted image to the presentation image generation unit 14.

The user instruction from the control unit 13 can be a parameter related to adjustment of a grayscale for optimization, and can also be an image range to be noted for the adjustment of the grayscale or information of a site to be noted for the adjustment of the grayscale. When the image processing unit 12 receives the image range or the information of the site to be noted, a parameter of image adjustment that is likely to cause the target to be noted to be easily visible is computed, information related to the image adjustment such as a result thereof is transmitted to the control unit 13 as adjustment information, and then the adjustment of the image is performed. It should be noted that, upon receiving the information related to the site that is set as a target to be noted, the image processing unit 12 detects the corresponding site within the input image, and computes the parameter of the image adjustment.

The control unit 13 is configured as, for example, a central processing unit (CPU) or the like, and controls each unit according to a program stored in the storage unit 17. The user input unit 16 is configured as, for example, a mouse serving as a pointing device, a keyboard, or the like. A user manipulates the user input unit 16 to perform input for adjusting a presented eye-fundus image while checking an image for display presented in the image presentation unit 15. A result of a user input using the user input unit 16 is transferred to the control unit 13.

This user input, for example, a position pointed to with the mouse or information on clicking, is converted into user input interpretation by the control unit 13 based on a presentation image presented to the user. The control unit 13 retains a grayscale adjustment mode of the image or grayscale adjustment information of the past, decides image processing to be performed by adding information of the user input interpretation to the information, and transmits a result thereof to the image processing unit 12 as a user instruction. In addition, based on the grayscale adjustment mode or the grayscale adjustment information of the past and the information of the user input interpretation, the control unit 13 decides a menu or the like as a graphical user interface (GUI) to be presented in a presentation image, and transmits the menu or the like to the presentation image generation unit 14 as an instruction of display for user input.

The presentation image generation unit 14 receives the adjusted image from the image processing unit 12, combines the image with the image for user input based on the instruction of the display for user input from the control unit 13, and then outputs the result to the image presentation unit 15 as a presentation image. The image presentation unit 15 configured by a liquid crystal display (LCD), a speaker, and the like presents the presentation image received from the presentation image generation unit 14.

The storage unit 17 is configured as a hard disk, a semiconductor memory, or the like, and stores programs, data, and the like of the control unit 13, the image processing unit 12, and the like according to necessity.

[Image Display Process]

Figure 2:
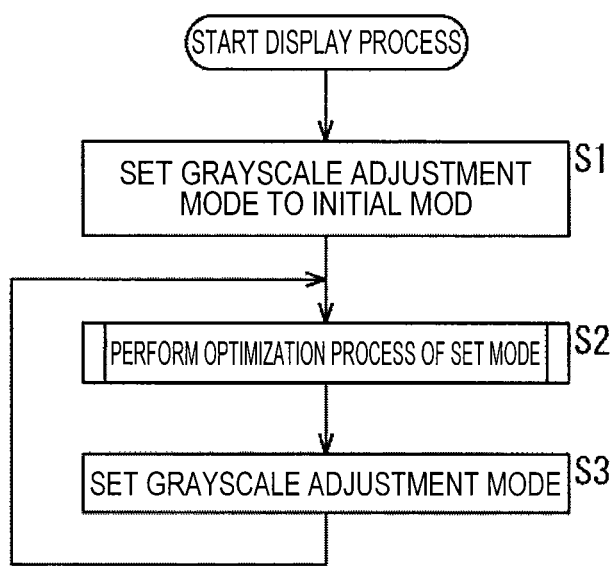
FIG. 2 is a flow chart describing an example of a display process.

Next, an image display process of the eye-fundus image output device 1 will be described. FIG. 2 is a flow chart describing an example of a display process. This process starts when the user manipulates the user input unit 16 to instruct that the process begin.

The control unit 13 sets a grayscale adjustment mode to an initial mode in Step S1. It is of course possible to set the grayscale adjustment mode to another mode.

The image processing unit 12 executes an optimization process of the set mode in Step S2. Although details thereof will be described below with reference to FIG. 4, the optimization process of the predetermined grayscale adjustment mode is accordingly executed. In this case, the optimization process of the initial mode is executed.

The control unit 13 sets a grayscale adjustment mode in Step S3. Specifically, when it is determined that a change of the grayscale adjustment mode has been instructed in Step S32 of FIG. 4 to be described below, the process of Step S3 is executed. In other words, when the user instructs a change of the grayscale adjustment mode, the changed grayscale adjustment mode is set.

Then, the process returns to Step S2, and the optimization of the grayscale adjustment mode set in Step S3 is executed.

The above process is repeatedly executed until an end of the process is instructed.

[Configuration of an Image Processing Unit]

Figure 3:
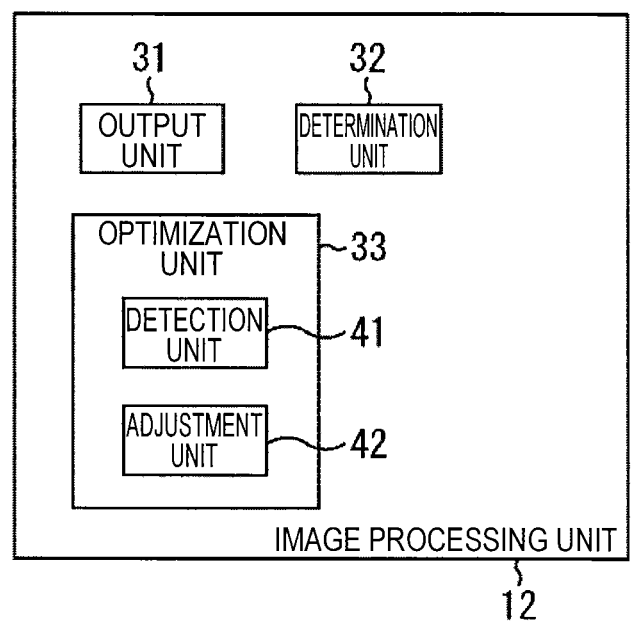
FIG. 3 is a block diagram illustrating a functional configuration of an image processing unit.

The image processing unit 12 which executes the process of Step S2 of FIG. 2 has a configuration with which various functions shown in FIG. 3 are executed. FIG. 3 is a block diagram illustrating a functional configuration of the image processing unit 12.

An output unit 31 outputs an adjusted image. A determination unit 32 executes various determination processes. An optimization unit 33 which executes the optimization process of an image has a detection unit 41 and an adjustment unit 42. The detection unit 41 detects a predetermined region from an image. The adjustment unit 42 adjusts the grayscale of the image in order to optimize the image.

[Optimization Process of a Set Mode]

Figure 4:
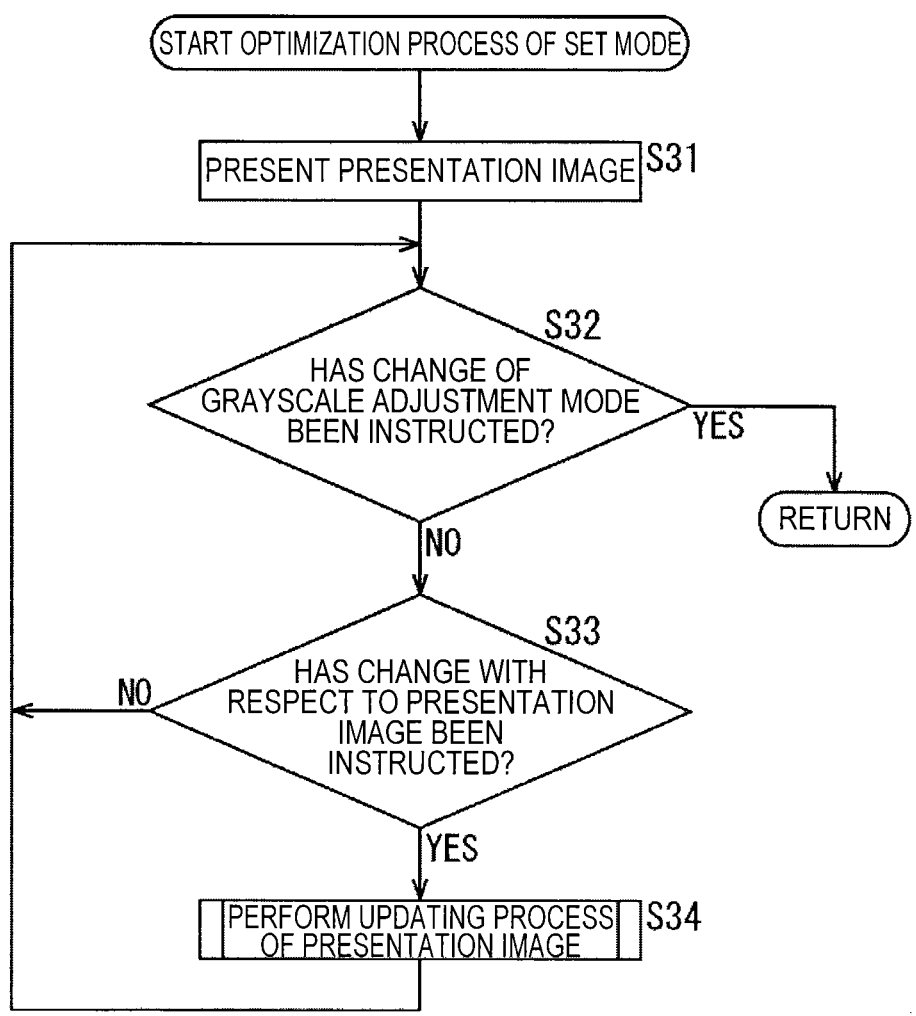
FIG. 4 is a flow chart describing an optimization process of a set mode.

Next, the optimization process of the set mode of Step S2 of FIG. 2 will be described. FIG. 4 is a flow chart describing the optimization process of the set mode of Step S2 of FIG. 2.

From now on, the optimization process of the set mode of FIG. 4 will be described on the assumption that the initial mode has been set in Step S1 of FIG. 2.

The output unit 31 of the image processing unit 12 presents a presentation image in Step S31. Specifically, the image acquisition unit 11 photographs the eye fundus of the subject eye 21 of the examinee and inputs the image to the image processing unit 12. The adjustment unit 42 of the optimization unit 33 adjusts the image to be an image with brightness and contrast of the initial mode set in advance. The output unit 31 outputs the image adjusted (in other words, optimized) by the adjustment unit 42 to the presentation image generation unit 14 as an adjusted image.

The presentation image generation unit 14 also receives an input of an instruction of GUI generation from the control unit 13. The presentation image generation unit 14 generates a necessary GUI for the user to control image display in compliance with the instruction, and then combines the GUI with the adjusted image. The combined image is supplied to the image presentation unit 15 and then presented. It should be noted that the user here in many cases is not a general photographer but a doctor who makes a medical determination based on a presentation image.

Figure 5:
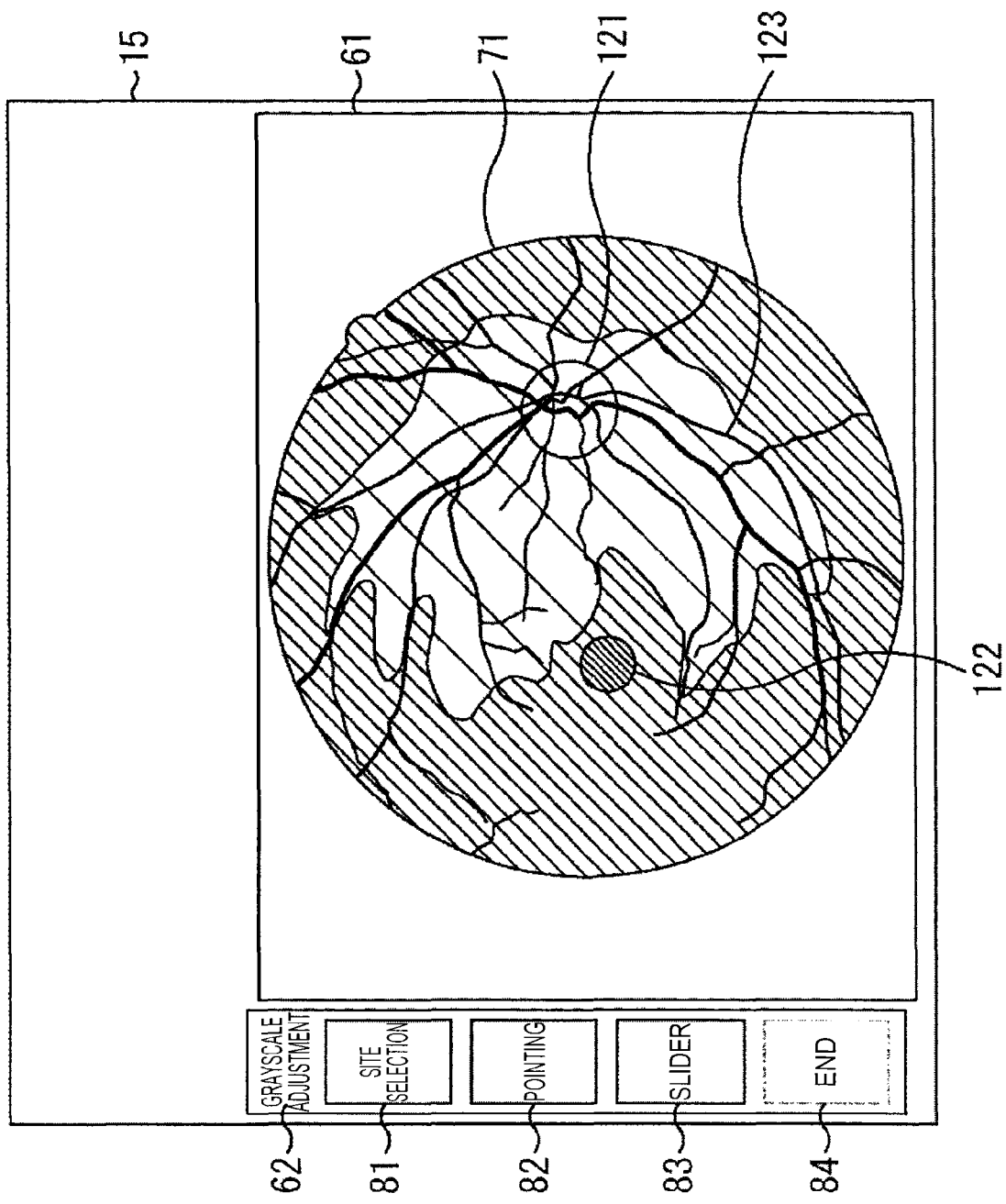
FIG. 5 is a diagram illustrating an example of a presentation image in an initial mode.

FIG. 5 is a diagram illustrating an example of a presentation image displayed on the image presentation unit 15 in the initial mode as described above. In the example of FIG. 5, an image 71 of a fundus supplied from the image processing unit 12 to a region 61 is displayed. In the image 71, an optic disc portion 121, a macular area 122, blood vessels 123, and the like are shown. In a region 62, manipulation units manipulated by a user to perform adjustment of the grayscale are displayed. In the case of the example, three grayscale adjustment modes are prepared, and thus as the manipulation units, a site selection button 81, a pointing button 82, and a slider button 83 are displayed. In addition, an end button 84 is displayed.

The site selection button 81 is manipulated when a site selection mode is to be set. The pointing button 82 is manipulated when a pointing mode is to be set. The slider button 83 is manipulated when a slider mode is to be set. The end button 84 is manipulated to return a grayscale adjustment mode to the initial mode.

The manipulation units can also be set as icons displaying figures, images, and the like which remind the user of such modes, rather than displaying letters.

Returning to FIG. 4, in the state in which the image is presented on the image presentation unit 15 in Step S31 as described above, the determination unit 32 determines whether a change of the grayscale adjustment mode has been instructed in Step S32. The user manipulates the site selection button 81 when the site selection mode is set, manipulates the pointing button 82 when the pointing mode is set, and manipulates the slider button 83 when the slider mode is set. The determination unit 32 determines which button has been manipulated.

When no button has been manipulated, the determination unit 32 determines whether a change with respect to the presentation image has been instructed in Step S33. The instruction of the change with respect to the presentation image refers to, for example, an instruction based on a manipulation of an optic disc portion button 111, a macular area button 112, a medium-large blood vessel portion 113, and the like of FIG. 6 to be described below, or an instruction based on a manipulation of sliders 204, 204-1, 204-2, or the like of FIGS. 14, 17, and 18.

In the initial mode, an instruction of a change with respect to the presentation image is set not to be received. Thus, in the initial mode, Step S33 is determined to be NO at all times, and thus the process returns to Step S32. As a result, when the user manipulates any mode button in the initial mode, Step S32 is determined to be YES, the process proceeds to Step S3 of FIG. 2, and thus the grayscale adjustment mode selected by the user is set.

[Site Selection Mode]

Now, it will be assumed that the user has manipulated the site selection button 81 to select a predetermined site in the initial mode. In this case, it is determined in Step S32 of FIG. 4 that a change of the grayscale adjustment mode has been instructed. Then, the process proceeds to the process of Step S3 of FIG. 2, and then the control unit 13 sets the site selection mode selected by the user as the grayscale adjustment mode. Then, the process returns to Step S2, and the optimization process of the set mode of FIG. 4 is executed on the site selection mode.

Figure 6:
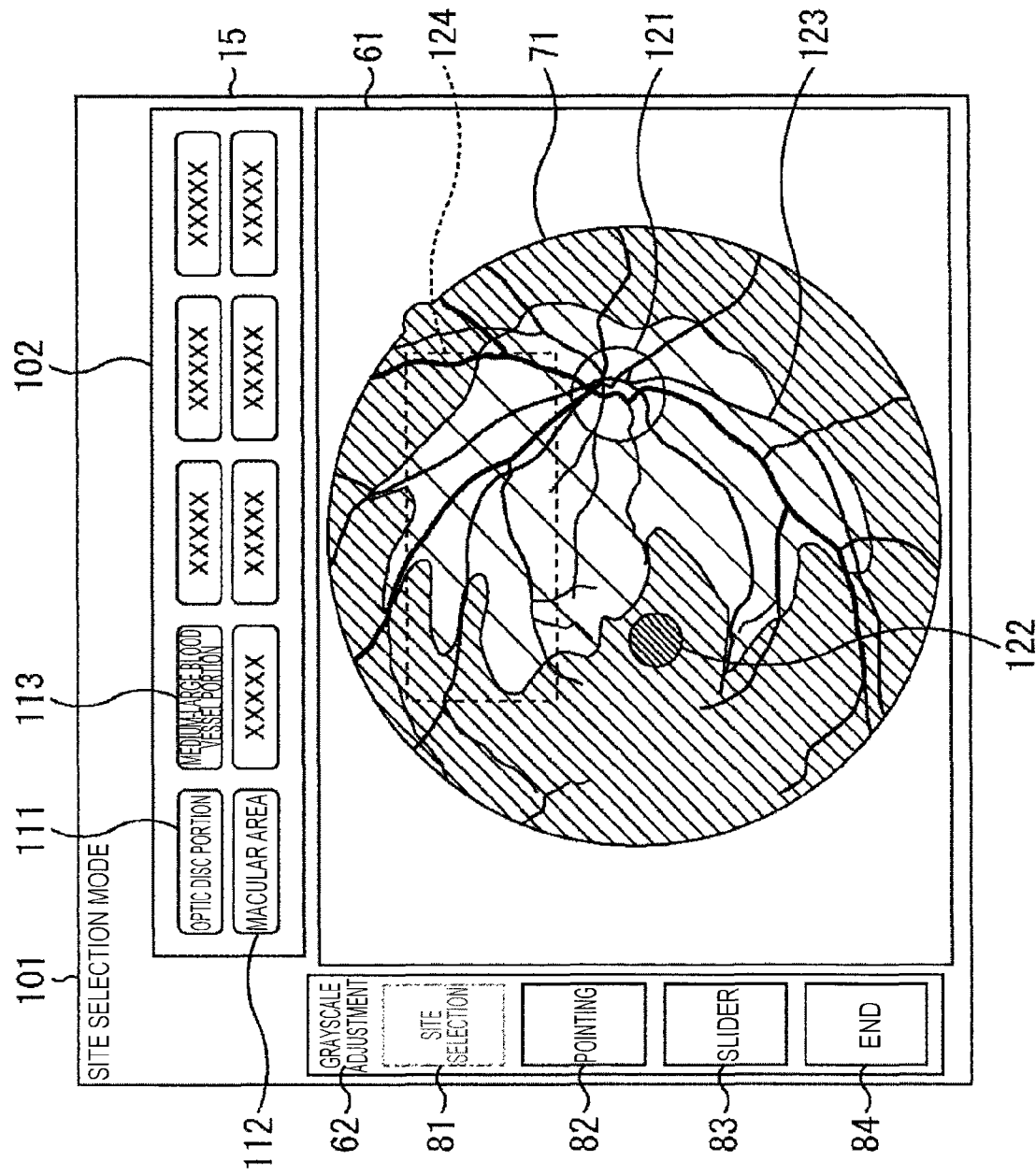
FIG. 6 is a diagram illustrating an example of a presentation image in a site selection mode.

In Step S31 in the site selection mode, the control unit 13 causes, for example, a GUI screen illustrated in FIG. 6 to be displayed. FIG. 6 is a diagram illustrating an example of a presentation image in a site selection mode. In the example of FIG. 6, the letters that refer to the site selection mode that is the selected grayscale adjustment mode are displayed in a region 101. In addition, buttons named after sites selected by the user are displayed in a region 102. In this example, buttons including the optic disc portion button 111, the macular area button 112, the medium-large blood vessel portion button 113, and the like are displayed. These buttons can also be prepared as icons.

The optic disc portion button 111 is manipulated when a site to be noted is set to the optic disc portion 121. The macular area button 112 is manipulated when the site to be noted is set to the macular area 122. The medium-large blood vessel portion button 113 is manipulated when the site to be noted is set to a medium-large blood vessel portion 124.

The determination unit 32 determines whether a change of the grayscale adjustment mode has been instructed in Step S32 of FIG. 4. When the change of the grayscale adjustment mode has not been instructed, the determination unit 32 determines in Step S33 whether a change with respect to the presentation image has been instructed. Since the site selection mode has been set now, the user selects any of the buttons displayed in the region 102 to select a site. That is to say, any button of the optic disc portion button 111, the macular area button 112, the medium-large blood vessel portion button 113, and the like is manipulated. When any button has been manipulated, it is determined in Step S33 that the change of the grayscale adjustment mode has been instructed, and the updating process of the presentation image of Step S34 is executed.

Figure 7:
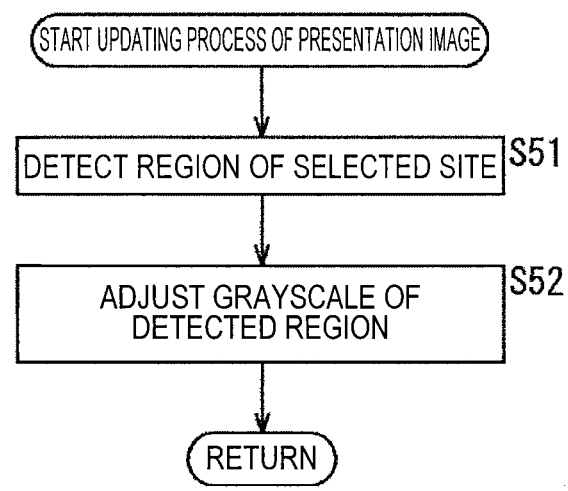
FIG. 7 is a flow chart describing an updating process of the presentation image in the site selection mode.

Herein, the updating process of the presentation image in the site selection mode will be described with reference to FIG. 7. FIG. 7 is a flow chart describing the updating process of the presentation image in the site selection mode of Tep S34.

The detection unit 41 of the optimization unit 33 detects the region of a selected site in Step S51. For example, when the optic disc portion button 111, the macular area button 112, or the medium-large blood vessel portion button 113 is manipulated, the optic disc portion 121, the macular area 122, or the medium-large blood vessel portion 124 is detected.

The adjustment unit 42 adjusts in Step S52 the grayscale of the area detected in the process of Step S51. That is to say, at least one or both of brightness and contrast of the image is adjusted to a predetermined value. The adjusted image is supplied to the presentation image generation unit 14 by the output unit 31, and then presented on the image presentation unit 15.

Figure 8:
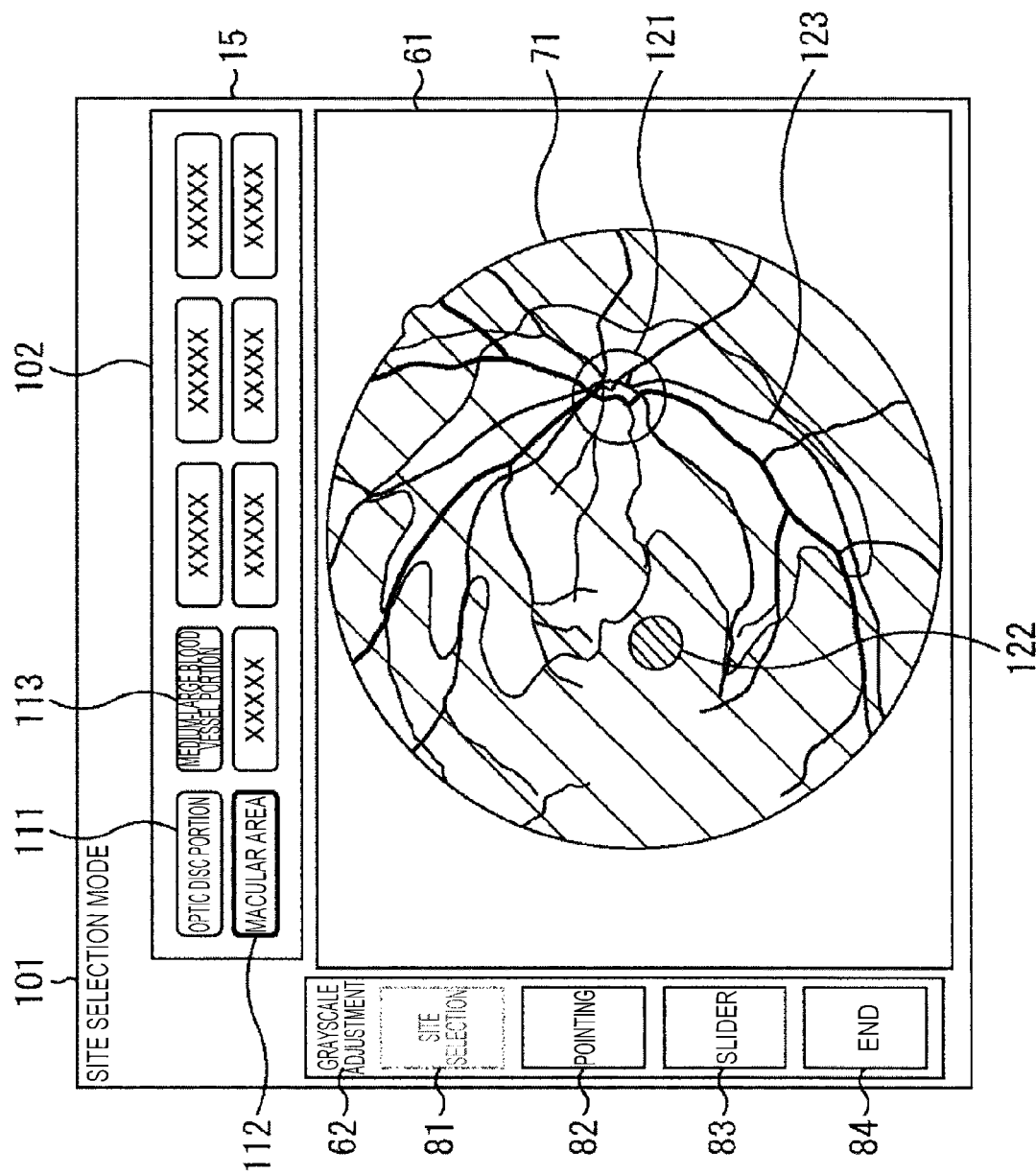
FIG. 8 is a diagram illustrating an example of a presentation image of which a grayscale has been adjusted.

FIG. 8 is a diagram illustrating an example of the presentation image of which the grayscale has been adjusted when the macular area button 112 has been selected. As is obvious from comparison of the image 71 of FIG. 8 to the image 71 of FIG. 6, while the macular area 122 is dark and difficult to view in the image 71 of FIG. 6 (that is, the input image), in the image 71 of FIG. 8, the macular area 122 is bright and easy to view.

As described above, with only a simple manipulation of selecting a site, an image of the site is optimized and presented, and interpretation thereof becomes easy. Particularly, even when there are a plurality of sites to be noted, the manipulation is easy because each of the sites is only selected. In addition, since a selected site is set to be optimized, interpretation can be performed quickly in comparison to when an optimized image is prepared and stored in advance. In other words, it is possible to perform interpretation on an image obtained from photographing in real time. Thus, management and complication at the time of storage of a fundus image can be reduced, and data volume can be suppressed from increasing.

[Adjustment of Gain and Contrast]

Figure 9:
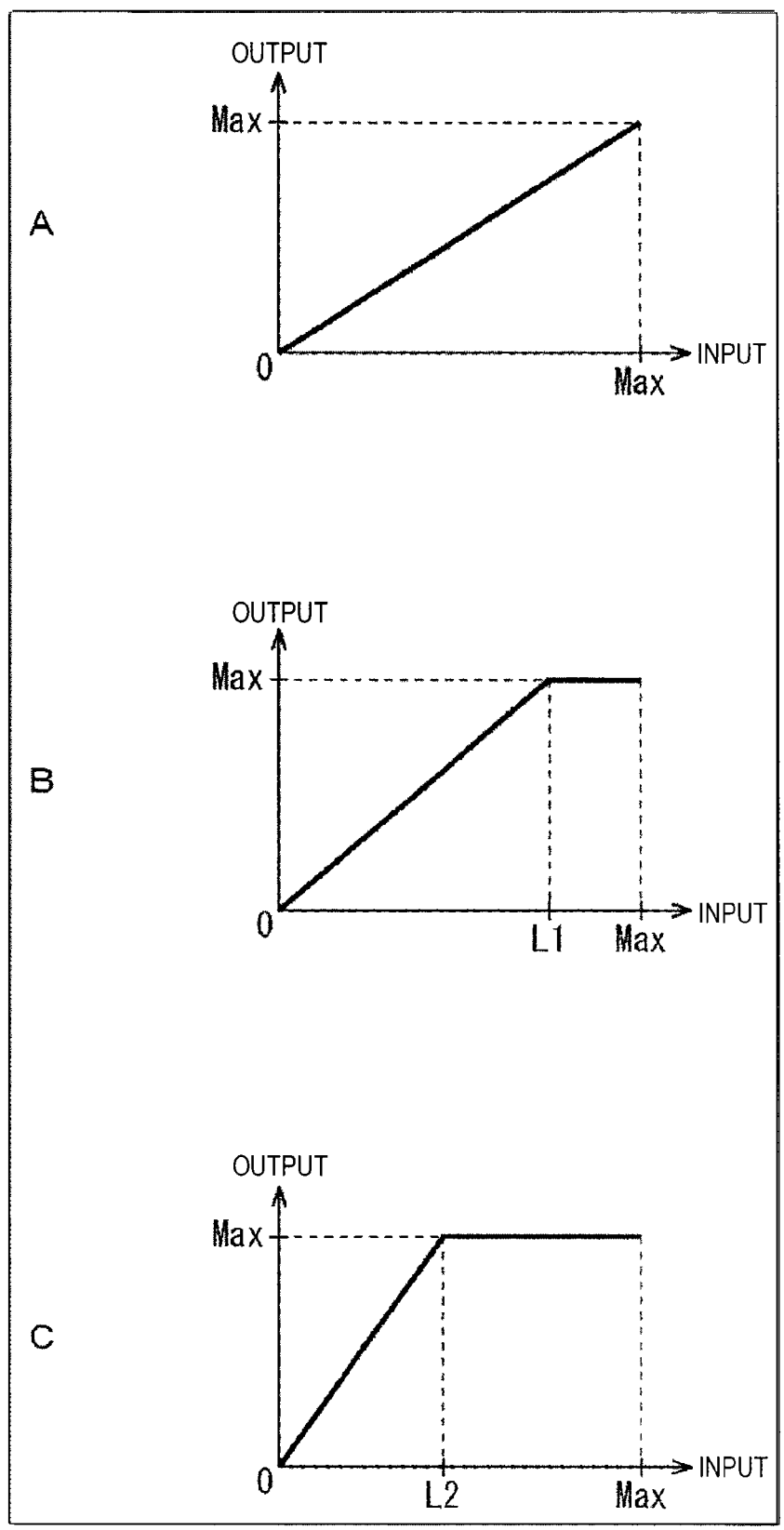
FIG. 9 is a diagram illustrating characteristics of gain adjustment.

When brightness is adjusted, specifically gain is adjusted. FIG. 9 is a diagram illustrating characteristics of gain adjustment. A of FIG. 9 shows the characteristic when small gain is set, in which the level of an output image changes in direct proportion to the level of an input image. B of FIG. 9 shows the characteristic when default gain is set, in which, while the level of the input image reaches a predetermined threshold value L1, the level of the output image changes in direct proportion to the level of the input image. When the level of the input increases greater than the threshold value L1, the level of the output image is fixed to its maximum value. In the initial mode, the image adjustment is performed with the characteristic of B of FIG. 9.

On the other hand, C of FIG. 9 shows the characteristic when large gain is set, in which, while the level of the input image reaches a predetermined threshold value L2, the level of the output image changes in direct proportion to the level of the input image. When the level of the input is greater than the threshold value L2, the level of the output image is fixed to its maximum value. In addition, the threshold value L2 is smaller than the threshold value L1. When the macular area button 112 is manipulated and thus the macular area 12 is set as a site to be noted, image adjustment is performed with the characteristic of C of FIG. 9. That is to say, since the characteristic of C of FIG. 9 causes a dark region to appear bright, the macular area 122 that is darker than the optic disc portion 121 is expressed in a bright and easy-to-view state. The bright optic disc portion 121 becomes complete white, but this does not matter because the current site to be noted is the macular area 122.

It should be noted that, when large gain is set as illustrated in C of FIG. 9, for example, a relatively low level of the input image is output as a maximum level in an adjusted image. In order to set the quality of the adjusted image to be easy for diagnosis even in the above case, it is desirable for the dynamic range of the input image to be sufficiently wide.

That is to say, when an input image of which each pixel is expressed with 8 bits is displayed on a display that enables 8-bit grayscale display, for example, if the characteristic shown in A of FIG. 9 is used, the 8 bits of the input image can be used as 8 bits to be supplied to the display without change. On the other hand, when the characteristic shown in C of FIG. 9 is used, a partial range of the 8 bits of the input image is enlarged to 8 bits and then supplied to the display. Thus, the grayscale has missing parts in the presentation image, and thereby degradation of image quality, for example, a false contour or the like, occurs. In order to avoid such a situation, when display is performed on a display which enables 8-bit grayscale display, for example, it is desirable to use an image having a wide dynamic range in which several bits are added to the LSB side so that the grayscale of the input image can be finely segmented with respect to the 8 bits.

Figure 10:
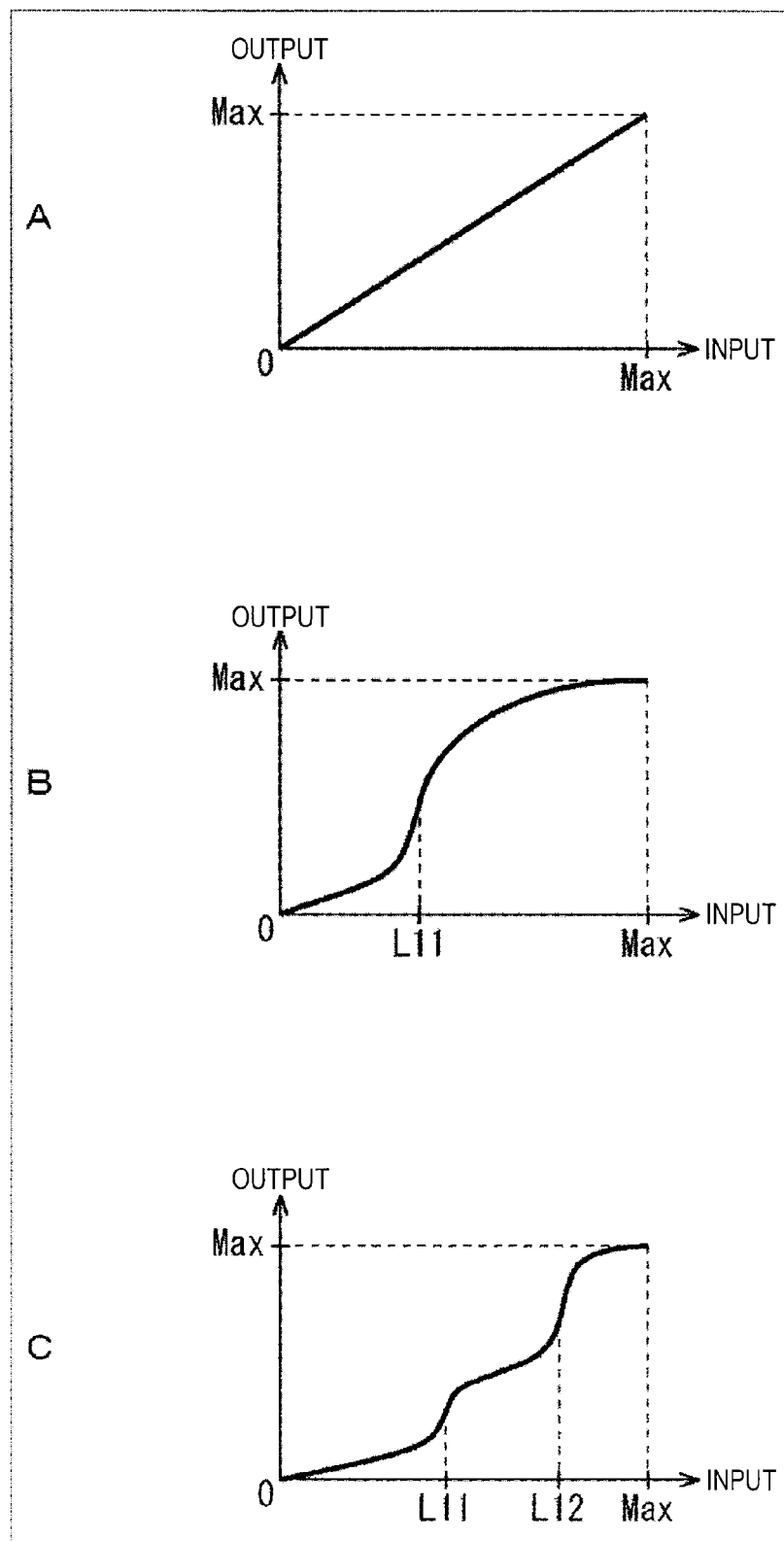
FIG. 10 is a diagram illustrating characteristics of contrast adjustment.

FIG. 10 is a diagram illustrating characteristics of contrast adjustment. A of FIG. 10 shows the characteristic when contrast is not adjusted, in which the level of an output image changes in direct proportion to the level of an input image. B of FIG. 10 shows the characteristic when a site to be noted is made easily visible, in which, while the level of the input image reaches a predetermined threshold value L11, the level of the output image changes substantially in direct proportion to the level of the input image. However, the level of the input sharply increases in the vicinity of the threshold value L11 (the characteristic becomes steep). This means that a larger number of grayscales are allocated to brightness of the vicinity of the threshold value L11 of the input image and then image adjustment is performed. When brightness of the input image becomes higher than the threshold value L11, the level of the output image converges on its maximum value. When the macular area 122 is a site to be noted, image adjustment is performed with this characteristic of B of FIG. 10. That is to say, brightness of the macular area 122 of the input image is set in the vicinity of the threshold value L11.

On the other hand, C of FIG. 10 shows the characteristic when two sites to be noted are set, in which, while the level of the input image reaches the predetermined threshold value L11, the level of the output image changes substantially in direct proportion to the level of the input image. However, when the level of the input sharply increases in the vicinity of the threshold value L11 (the characteristic becomes steep) and further increases, the level of the output image increases substantially in direct proportion to the level of the input image. In addition, when the level of the input sharply increases in the vicinity of a threshold value L12 (L12>L11) (the characteristic becomes steep) and further increases, it converges on its maximum value. That is to say, in this case, a larger number of grayscales are allocated to brightness of the vicinity not only of the threshold value L11 of the input image but also of the threshold value L12 and then image adjustment is performed.

When both of the macular area 122 and the optic disc portion 121 are set as sites to be noted, for example, image adjustment is performed with the characteristic of C of FIG. 10. Contrast of the macular area 122 that is darker is adjusted in the vicinity of the threshold value L11, and contrast of the optic disc portion 121 that is brighter is adjusted in the vicinity of the threshold value L12.

With the operation described above, image processing for the selected site to be noted is executed in Step S34 of FIG. 4, and then the image is displayed. That is to say, when the optic disc portion button 111 or the medium-large blood vessel portion button 113 is manipulated, a site corresponding to that button is set as a site to be noted, and image adjustment is performed for the site.

It should be noted that an image that has not undergone so-called gamma correction for correcting conversion of the grayscale that is attributable to a display may be input as an input image and then the process of gamma correction may be performed on the adjusted image in the presentation image generation unit 14. In addition, an image that has undergone gamma correction may be input as an input image and then the process of gamma correction may not be performed in the presentation image generation unit 14. Furthermore, when an image that has undergone gamma correction is used as an input image, the level thereof may be caused to return once to the image level prior to gamma correction before grayscale adjustment is performed in the image processing unit 12, and then after the grayscale adjustment is performed, gamma correction may be performed on the adjusted image in the presentation image generation unit 14.

[Pointing Mode]

Next, a process performed when the user manipulates the pointing button 82 will be described. In this case, it is determined in Step S32 of FIG. 4 that a change of the grayscale adjustment mode has been instructed, and the pointing mode is set in Step S3 of FIG. 2. Then, an image of the pointing mode as illustrated in FIG. 11 is displayed in Step S31 of FIG. 4.

Figure 11:
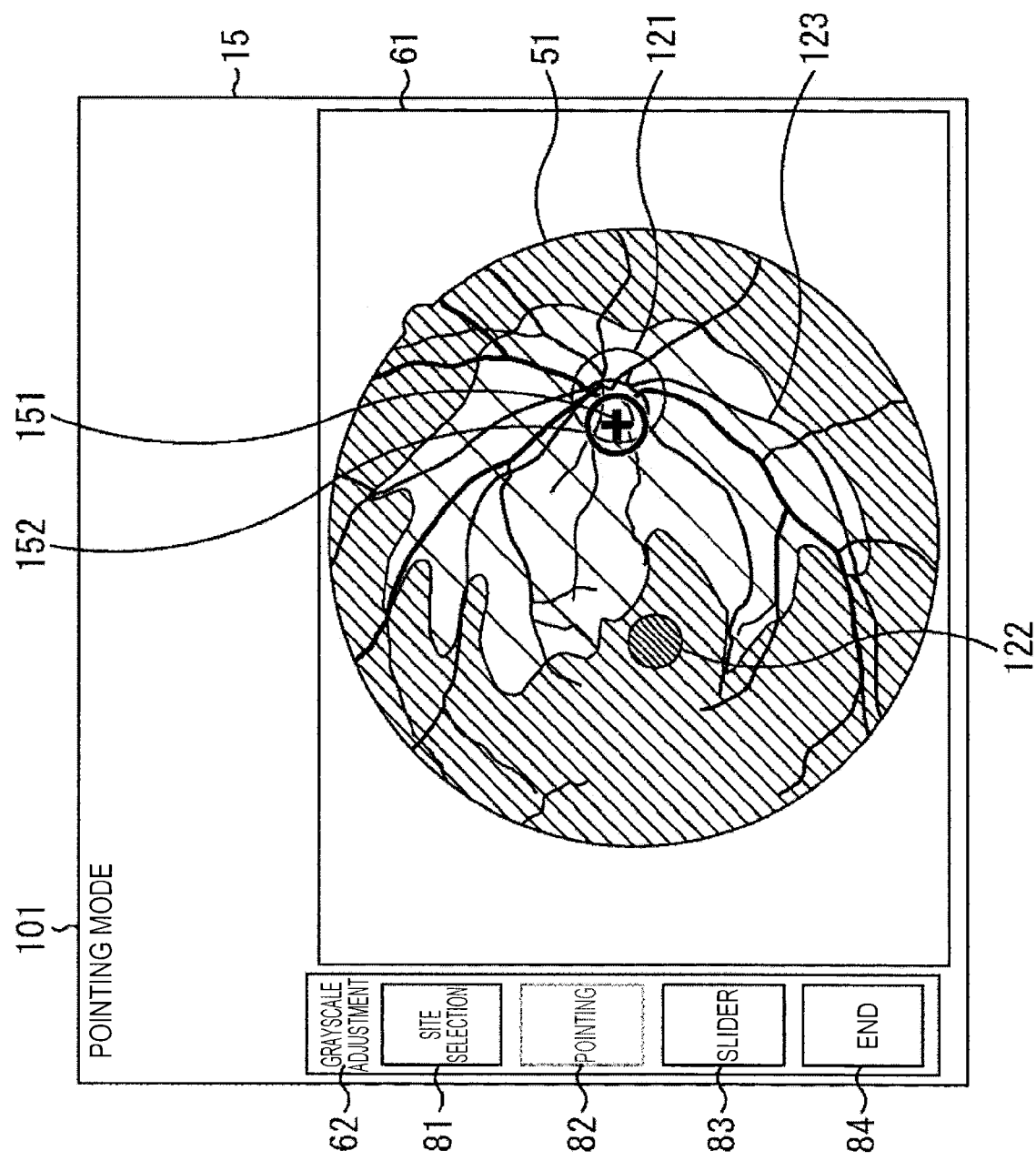
FIG. 11 is a diagram illustrating an example of a presentation image in a pointing mode.

FIG. 11 is a diagram illustrating an example of the presentation image in the pointing mode. In the example of FIG. 11, the letters that refer to the pointing mode are displayed in the region 101. In addition, a cross-shaped pointer 151 is displayed in a region 61, and a circular mark 152 that indicates the range from the center of the pointer 151 is displayed as well. The mark 152 indicates the range within which image adjustment (optimization) is performed. The mark 152 can be an arbitrary shape, for example, a rectangular shape.

The user manipulates the user input unit 16 to move the pointer 151 to the center position of an arbitrary range for which image adjustment is desired to be performed. Then, completion of position designation is ordered by performing a clicking manipulation or the like. At this time, the change with respect to the presentation image is determined to have been instructed in Step S33 of FIG. 4, and the updating process of the presentation image of Step S34 is executed. The process of this case will be described with reference to FIG. 12.

Figure 12:
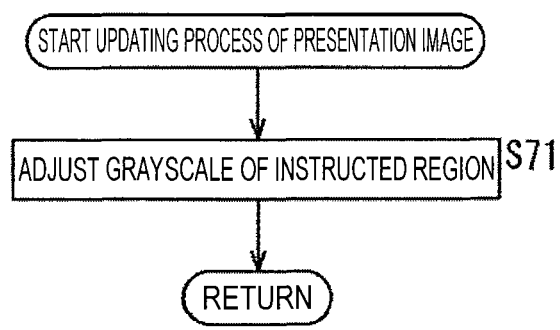
FIG. 12 is a flow chart describing an updating process of the presentation image in the pointing mode.

FIG. 12 is a flow chart describing the updating process of the presentation image in the pointing mode. The adjustment unit 42 adjusts the grayscale of the instructed area in Step S71. In other words, in order to set the image of the range indicated by the mark 152 to be more easily visible, at least one or both of brightness and contrast thereof is adjusted (i.e., optimized).

Figure 13:
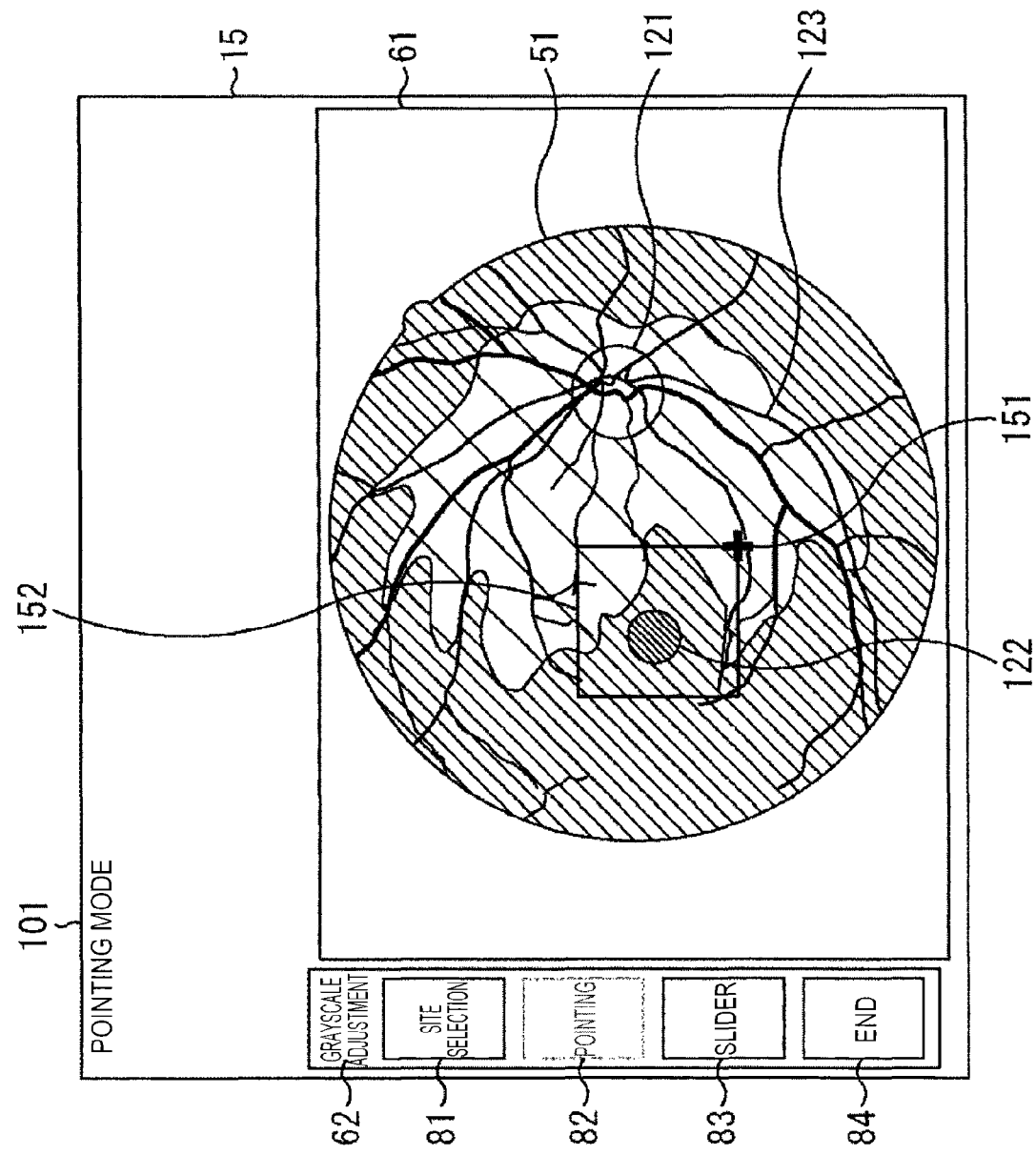
FIG. 13 is a diagram illustrating an example of a presentation image in a pointing mode.

In the example of FIG. 11, the mark 152 is set to have a pre-decided size; however, it is possible to set an arbitrary range thereof as illustrated in FIG. 13. FIG. 13 is a diagram illustrating another example of the presentation image in the pointing mode. In the example of FIG. 13, a rectangular range having two points designated by the user with the pointer 151 as diagonal points is indicated as the mark 152, and the inside of the range is set as a target of image adjustment.

As described above, with a simple manipulation of designating an arbitrary position, the image of the position is optimized and presented, and thus a spot other than the site to be noted prepared in advance is also easily observable.

[Slider Mode]

Next, a process performed when the user manipulates the slider button 83 will be described. In this case, it is determined in Step S32 of FIG. 4 that a change of the grayscale adjustment mode has been instructed, and the slider mode is set in Step S3 of FIG. 2. Then, an image of the slider mode as illustrated in FIG. 14 is displayed in Step S31 of FIG. 4.

Figure 14:
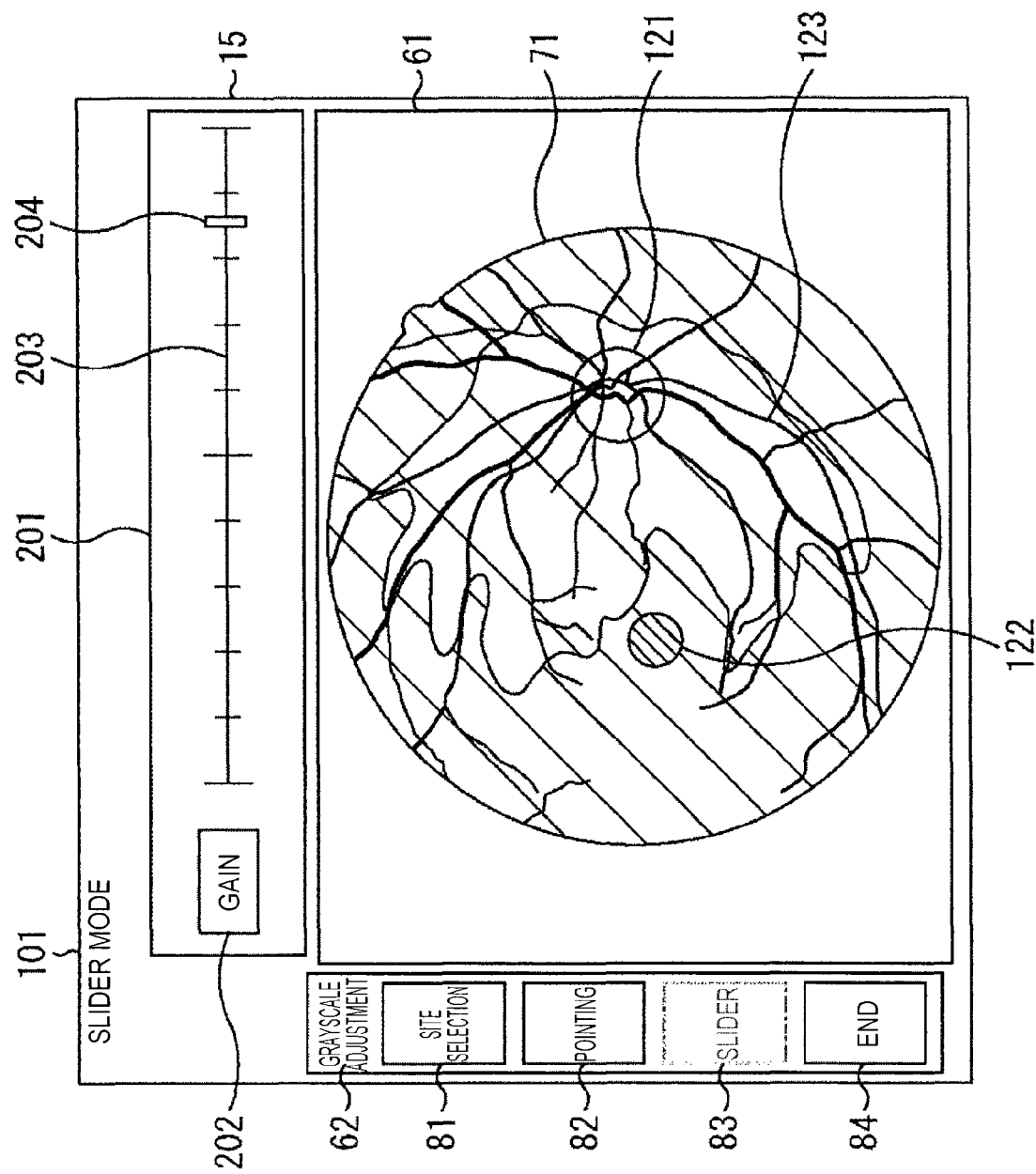
FIG. 14 is a diagram illustrating an example of a presentation image in a slider mode.

In the example of FIG. 14, the letters that refer to the slider mode are displayed in the region 101. In addition, a scale 203 is displayed in a region 201 and the letters that refer to gain which means information indicated by the scale 203 are displayed in a region 202 on the left side of the scale 203. A slider 204 is displayed on the scale 203. A position on the scale 203 of the slider 204 indicates the value of adjustment gain of the image 71 displayed in the region 61. In the example of FIG. 14, the ends on the left and right of the scale 203 correspond to the minimum and maximum values of adjustable values.

An initial position of the slider 204 can be caused to correspond to adjustment gain of the image of the previous mode. For example, when the mode transitions from the site selection mode illustrated in FIG. 8 to the slider mode, the slider 204 can be displayed at the position indicating the adjustment gain set for the image 71 of FIG. 8 on the initial screen of the slider mode illustrated in FIG. 14. Of course, a defined gain initial position with respect to the slider mode can also be set.

The user can move the slider 204 to an arbitrary position on the scale 203 by manipulating the user input unit 16. When the slider 204 serving as a manipulation unit is moved, it is determined in Step S33 of FIG. 4 that a change with respect to the presentation image has been instructed and then the updating process of the presentation image is executed in Step S34. The updating process of the presentation image of this case will be described with reference to FIG. 15.

Figure 15:
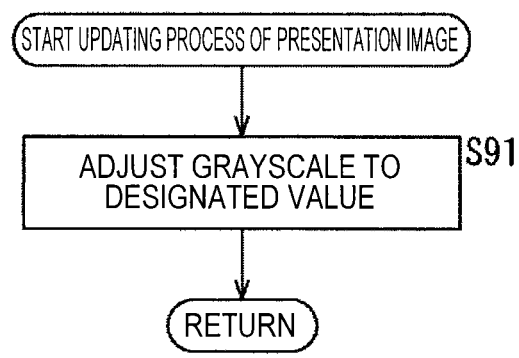
FIG. 15 is a flow chart describing an updating process of the presentation image in the slider mode.

FIG. 15 is a flow chart describing the updating process of the presentation image in the slider mode. The adjustment unit 42 adjusts the grayscale to a designated value in Step S91. In other words, gain of the image 71 is adjusted to the value of the position to which the user moved the slider 204 on the scale 203 (optimized to the value at which the image is to be optimized). The adjusted image is supplied to the image presentation unit 15 via the presentation image generation unit 14 and displayed.

By adjusting the position of the slider 204 with the operation described above, the image with brightness instructed by the user is displayed.

Figure 16:
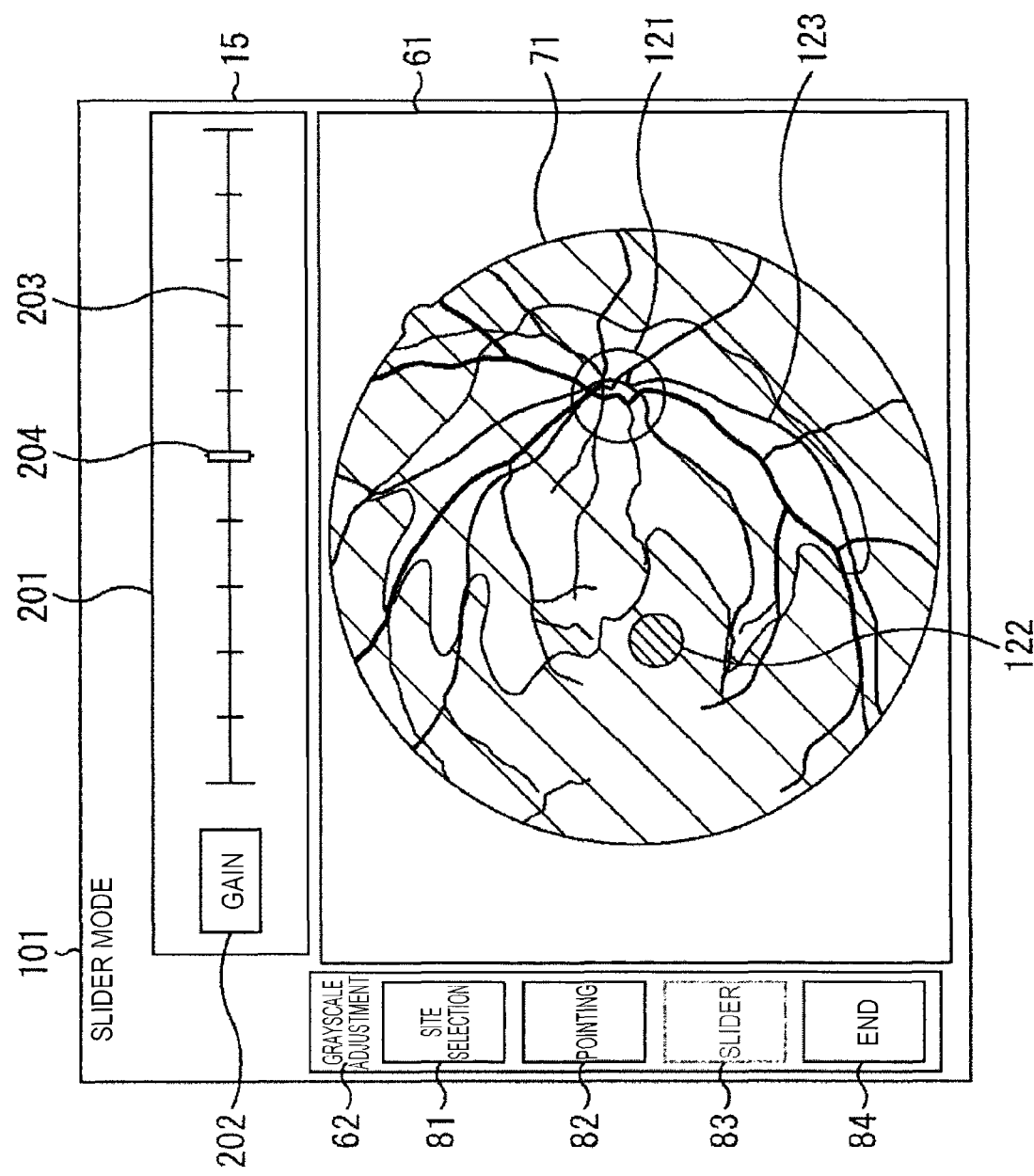
FIG. 16 is a diagram illustrating an example of a presentation image in a slider mode.

It is also possible to set the initial position of the slider 204 to a position at which fine adjustment for brightness is easy. FIG. 16 is a diagram illustrating another example of the presentation image in the slider mode. In the example of FIG. 16, the initial position of the slider 204 is set to the center of the scale 203. That is to say, in this case, when the mode transitions from the site selection mode illustrated in FIG. 8 to the slider mode, for example, the value of the adjustment gain set for the image 71 of FIG. 8 is set to the center of the scale 203. As a result, the slider 204 is displayed at the center of the scale 203. In this case, the ends on the left and right of the scale 203 do not necessarily correspond to the minimum and maximum values of adjustable values, but correspond to the minimum and maximum values of a predetermined range that can be expressed on the scale 203. Accordingly, the position of the slider 204 is between the direction in which the value increases and the direction in which the value decreases, and thus fine adjustment becomes easy in both directions.

Figure 17:
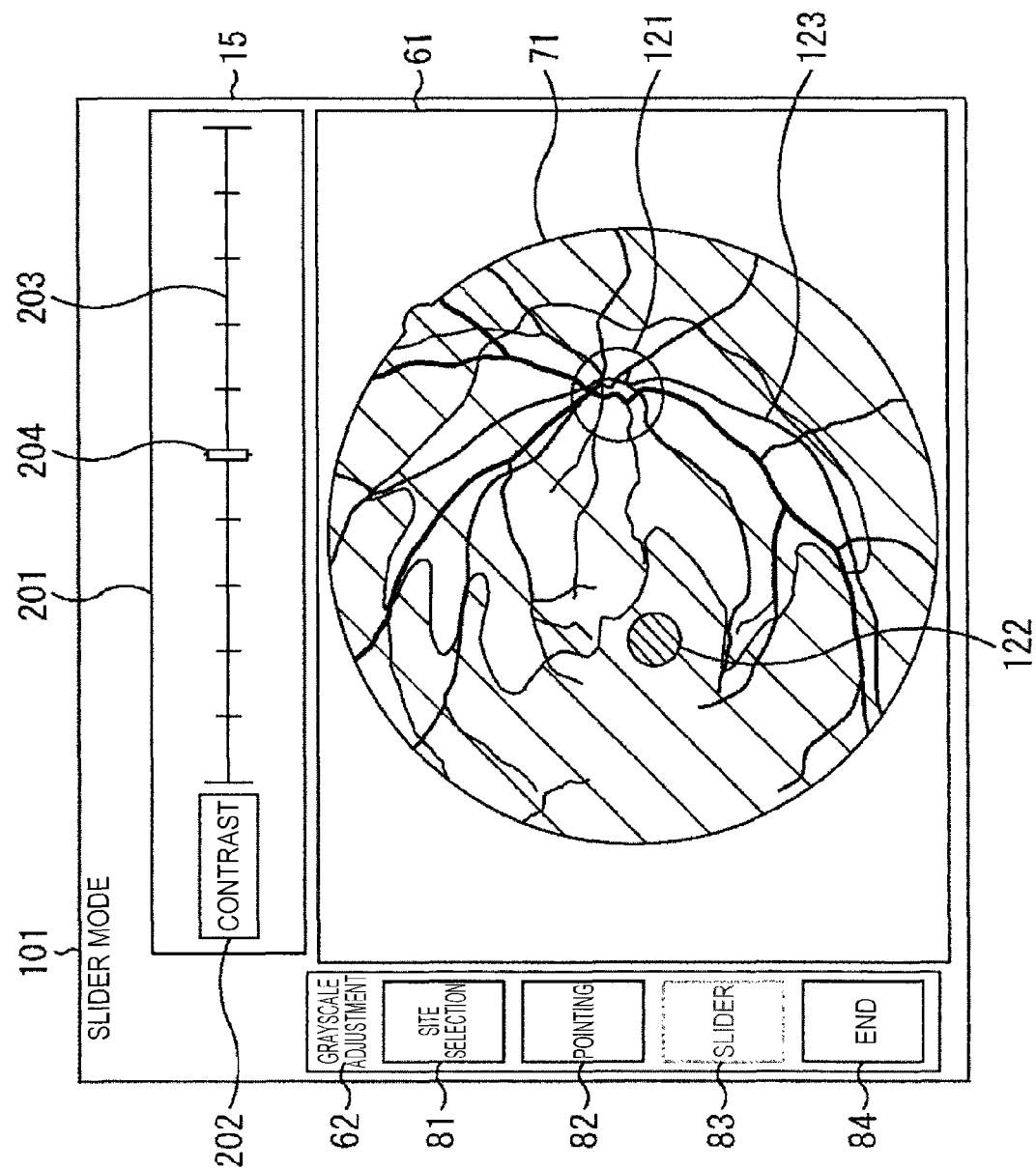
FIG. 17 is a diagram illustrating an example of a presentation image in a slider mode.

In the above description, brightness (i.e., gain) is set to be adjusted as image adjustment; however, contrast can also be set to be adjusted. FIG. 17 is a diagram illustrating an example of a presentation image in the slider mode. FIG. 17 is basically the same drawing as FIG. 16, but in the example of FIG. 17, the letters that refer to contrast rather than gain are displayed in the region 202. That is to say, the information indicated by the scale 203 is not brightness but contrast in FIG. 17. Also in this case, contrast can be adjusted to an arbitrary value as in the case of FIG. 16. For example, when the characteristic of B of FIG. 10 is employed in the slider mode of FIG. 17, a greater number of output grayscales can be allocated by moving the slider 204 slightly to the right side from the center in FIG. 17.

Figure 18:
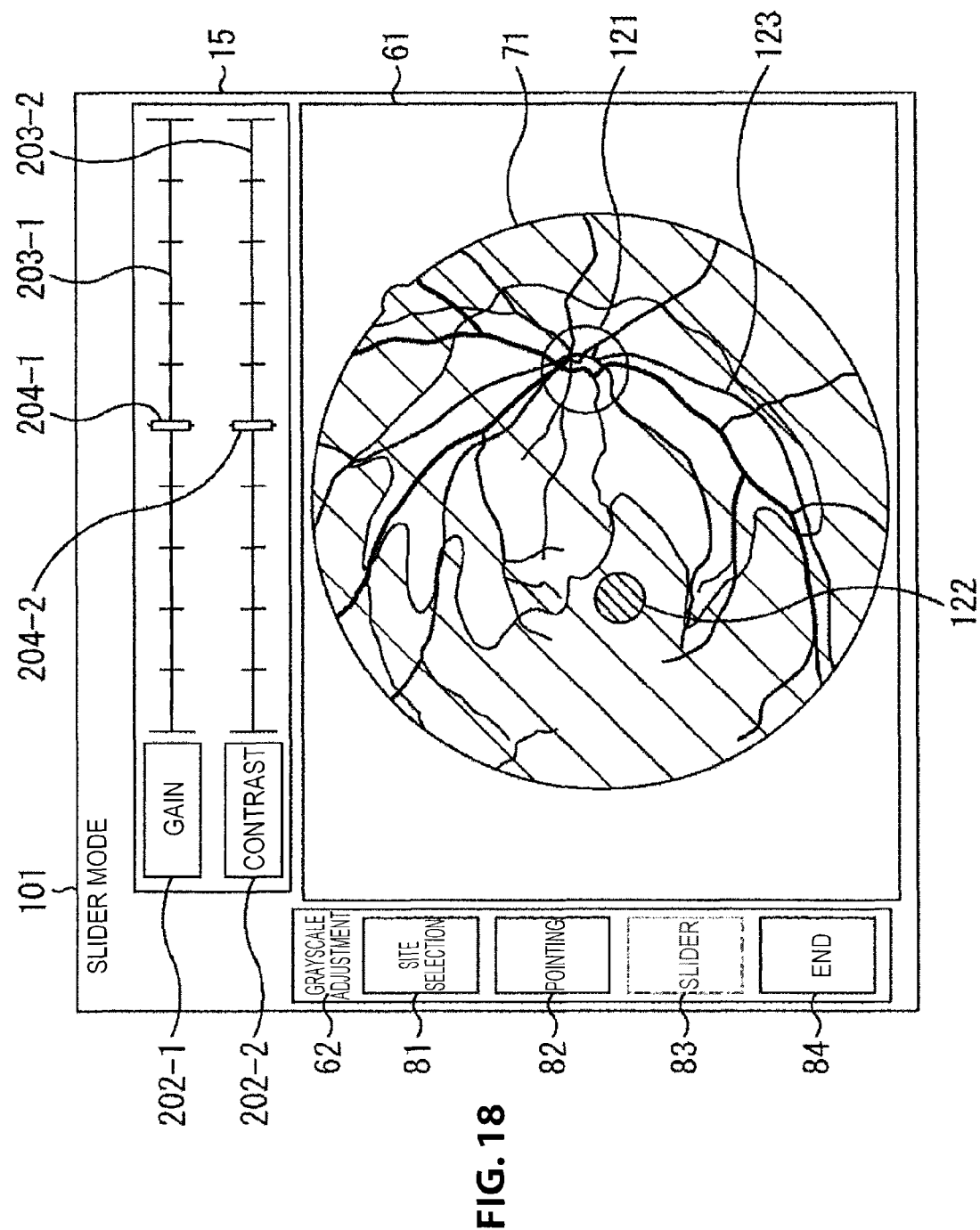
FIG. 18 is a diagram illustrating an example of a presentation image in a slider mode.

FIG. 18 is a diagram illustrating another example of the presentation image in the slider mode. In the example of FIG. 18, both of brightness (gain) and contrast are set to be adjustable. For this reason, a scale 203-1 and the slider 204-1 for adjusting brightness and a scale 203-2 and the slider 204-2 for adjusting contrast are displayed. In addition, the letters which refer to gain and contrast are displayed respectively in regions 202-1 and 202-2 corresponding to the scales 203-1 and 203-2.

In this example, both of brightness and contrast are adjustable by moving the respective sliders 204-1 and 204-2.

Since brightness and contrast are set to be finely adjustable in the slider mode as described above, even when brightness or the like of an image for easy observation differs depending on an interpreter, each interpreter can perform optimum adjustment.

[Application to a Program of the Present Technology]

The series of processes described above can be executed using hardware or executed using software.

When the series of processes is executed using software, a program included in the software is installed in a computer incorporated into dedicated hardware or various programs are installed in, for example, a general-purpose personal computer or the like that can execute various functions from a network or a recording medium.

A recording medium that includes such a program is configured as a removable medium including a magnetic disk (including a floppy disk), an optical disc (including a compact disk-read only memory (CD-ROM), and a DVD), a magneto-optical disk (including a Mini-Disk (MD)), a semiconductor memory, and the like that are distributed to provide the program to users, separate from the main body of a device. Alternatively, the recording medium can be configured as the storage unit 17 such as a flash ROM, a hard disk, or the like on which the program is recorded to be provided to users in a state in which it is incorporated into the main body of a device in advance.

It should be noted that the program executed by a computer may be a program in which the processes are performed in a time series manner in the order described in the present specification, and may be a program in which the processes are performed in parallel or at a necessary time point at which there is a call or the like.

It should be noted that embodiments of the present technology are not limited to the above-described embodiments, and can be variously modified within the scope not departing from the gist of the present technology.

For example, the present technology can adopt the configuration of cloud computing in which one function is divided and shared by a plurality of devices through a network for its process.

In addition, each step described in the above-described flow charts can be executed by one device and divided and executed by a plurality of devices.

Furthermore, when a plurality of processes are included in one step, the plurality of processes included in the one step can be executed by one device, or divided and executed by a plurality of devices.

[Other Configurations]

The present technology may also be configured as below.

(1)

An eye-fundus image output device including:

a selection unit configured to select a site of a presented eye-fundus image;

an optimization unit configured to optimize an image of the selected site; and an output unit configured to output an image in which the selected site has been optimized.

(2)

The eye-fundus image output device according to (1), further including:

a generation unit configured to generate a presentation image that is obtained by combining a GUI that includes a manipulation unit that is manipulated by a user when a plurality of grayscale adjustment modes are to be set with the eye-fundus image.

(3)

The eye-fundus image output device according to (1) or (2), wherein the GUI is capable of selecting, as the grayscale adjustment modes, at least two of a mode in which the site is selected, a mode in which an image of a predetermined range in the periphery of the designated position is optimized, or a mode in which an optimization value of the image is designated.

(4)

The eye-fundus image output device according to (3), wherein the GUI includes a manipulation unit that is manipulated when at least a macular area or an optic disc portion is selected as the site in the mode in which the site is selected.

(5)

The eye-fundus image output device according to (3) or (4), wherein, when the mode in which an image in the periphery of the designated position is optimized is selected as the grayscale adjustment mode, the optimization unit optimizes the image of the predetermined range in the periphery of the designated position.

(6)

The eye-fundus image output device according to (3), (4), or (5), wherein, when the mode in which an optimization value of the image is designated is selected as the grayscale adjustment mode, the optimization unit optimizes the image to have the designated optimization value.

(7)

The eye-fundus image output device according to any of (3) to (6), wherein, in the mode in which an optimization value of the image is designated, the GUI includes a manipulation unit that is manipulated when the optimization value is to be designated.

(8)

The eye-fundus image output device according to (7), wherein, in the mode in which an optimization value of the image is designated, the manipulation unit that is manipulated when the optimization value of the image is to be designated is disposed at a position corresponding to a value disposed in the immediately previous grayscale adjustment mode.

(9)

The eye-fundus image output device according to (7), wherein the position corresponding to the value disposed in the immediately previous grayscale adjustment mode of the manipulation unit is set to a center of a variable range.

(10)

The eye-fundus image output device according to any of (1) to (9), wherein the optimization is performed by adjusting brightness or contrast of the image.

(11)

An eye-fundus image output method including:
a selection step of selecting a site of a presented eye-fundus image;
an optimization step of optimizing an image of the selected site; and
an output step of outputting an image in which the selected site has been optimized.

(12)

A program causing a computer to execute processes, the processes including:
a selection step of selecting a site of a presented eye-fundus image;
an optimization step of optimizing an image of the selected site; and
an output step of outputting an image in which the selected site has been optimized.

REFERENCE SIGNS LIST 1 eye-fundus image output device
11 image acquisition unit
12 image processing unit
13 control unit
14 presentation image generation unit
15 image presentation unit
16 user input unit
17 storage unit

The invention claimed is:

1. An ophthalmic image output device comprising:
circuitry configured to
detect a selection within a site selection mode of a site of a presented ophthalmic image;
optimize an image of the selected site;
output an image in which the selected site has been optimized; and
generate a graphical user interface (GUI) corresponding to a received instruction,
wherein the circuitry is configured to receive a selection, via the GUI, of a grayscale adjustment mode in which a portion of an image of a predetermined range in the periphery of a designated position within the selected site is optimized according to the grayscale adjustment mode,
wherein the GUI is further configured to display a selectable menu of predefined regions of the ophthalmic image, and
wherein the portion of the image of a predetermined range in the periphery corresponds to the predefined regions.

2. The ophthalmic image output device according to claim 1, wherein the circuitry is further configured to:
generate a presentation image that is obtained by combining the GUI including a plurality of grayscale adjustment modes.

3. The ophthalmic image output device according to claim 2, wherein the circuitry is further configured to:
control the GUI to display the plurality of grayscale adjustment modes and a site selection mode in accordance with predefined parameters or in accordance with user input parameters.

4. The ophthalmic image output device according to claim 1, wherein the predefined regions of the ophthalmic image include at least one of a selection of a macular area an optic disc portion and a blood vessel portion.

5. The ophthalmic image output device according to claim 4, wherein, when the mode in which an image in the periphery of the designated position is optimized is selected as the grayscale adjustment mode, the circuitry optimizes the image of the predetermined range in the periphery of the designated position.

6. The ophthalmic image output device according to claim 5, wherein, when the mode in which an optimization value of the image is designated is selected as the grayscale adjustment mode, the circuitry optimizes the image to have the designated optimization value.

7. The ophthalmic image output device according to claim 6, wherein, in the mode in which an optimization value of the image is designated, the GUI includes a designation option to designate an optimization value.

8. The ophthalmic image output device according to claim 7, wherein, in the mode in which an optimization value of the image is designated, a default optimization value is set according to the preceding grayscale adjustment mode.

9. The ophthalmic image output device according to claim 8, wherein the default optimization value is set to a center of a variable range.

10. The ophthalmic image output device according to claim 9, wherein the optimization is performed by adjusting brightness or contrast of the image.

11. An ophthalmic image output method comprising:
   detecting, with circuitry, a selection within a site selection mode of a site of a presented ophthalmic image;
   optimizing, with the circuitry, an image of the selected site;
   outputting, with the circuitry, an image in which the selected site has been optimized;
   generating, with the circuitry, a graphical user interface (GUI) corresponding to a received instructions;
   receiving a selection, via the GUI, of a grayscale adjustment mode in which a portion of an image of a predetermined range in the periphery of a designated position within the selected site is optimized according to the grayscale adjustment mode; and
   displaying, via the GUI, a selectable menu of predefined regions of the ophthalmic image, the portion of the image of a predetermined range in the periphery corresponding to the predefined regions.

12. A non-transitory computer-readable storage medium including computer readable instructions thereon which when executed by a computer cause the computer to perform a method comprising:
   detecting a selection within a site selection mode of a site of a presented ophthalmic image;
   optimizing an image of the selected site;
   outputting an image in which the selected site has been optimized;
   generating, with the circuitry, a graphical user interface (GUI) corresponding to a received instruction;
   receiving a selection, via the GUI, of a grayscale adjustment mode in which a portion of an image of a predetermined range in the periphery of a designated position within the selected site is optimized according to the grayscale adjustment mode; and
   displaying, via the GUI, a selectable menu of predefined regions of the ophthalmic image, the portion of the image of a predetermined range in the periphery corresponding to the predefined regions.

* * * * *